(12) United States Patent  (10) Patent No.: US 7,973,921 B2
Silberstein et al.  (45) Date of Patent: Jul. 5, 2011

(54) DYNAMIC ILLUMINATION IN OPTICAL INSPECTION SYSTEMS

(75) Inventors: Shai Silberstein, Rishon-Le-Zion (IL); Tsafrir Avni, Shoam (IL)

(73) Assignee: Applied Materials South East Asia Pte Ltd., Sinapore (SG)

( * ) Notice: Subject to any disclaimer, the term of this patent is extended or adjusted under 35 U.S.C. 154(b) by 199 days.

(21) Appl. No.: 12/145,708

(22) Filed: Jun. 25, 2008

(65) Prior Publication Data

US 2009/0323052 A1  Dec. 31, 2009

(51) Int. Cl.
*G01N 21/00* (2006.01)
(52) U.S. Cl. .................. 356/237.3; 356/237.5
(58) Field of Classification Search ..... 345/237.1–237.5
See application file for complete search history.

(56) References Cited

U.S. PATENT DOCUMENTS

| | | | |
|---|---|---|---|
| 5,699,447 A | 12/1997 | Alumot et al. | |
| 6,366,315 B1 | 4/2002 | Drescher | |
| 6,608,676 B1 | 8/2003 | Zhao et al. | |
| 6,693,664 B2 | 2/2004 | Neumann | |
| 6,724,473 B2 | 4/2004 | Leong et al. | |
| 7,088,443 B2 | 8/2006 | Vaez-Iravani et al. | |
| 7,265,900 B2 | 9/2007 | Korngut et al. | |
| 7,274,444 B2 | 9/2007 | Furman et al. | |
| 2002/0044278 A1 | 4/2002 | Le | |
| 2004/0012775 A1 | 1/2004 | Kinney et al. | |
| 2004/0146295 A1 | 7/2004 | Furman et al. | |
| 2004/0169851 A1* | 9/2004 | Yang et al. | 356/237.2 |
| 2006/0066843 A1 | 3/2006 | Guetta et al. | |
| 2007/0013898 A1 | 1/2007 | Wolters et al. | |
| 2007/0229813 A1 | 10/2007 | Miyakawa et al. | |
| 2007/0268484 A1* | 11/2007 | Matsui | 356/237.3 |
| 2007/0273945 A1 | 11/2007 | Furman et al. | |
| 2008/0037933 A1 | 2/2008 | Furman et al. | |
| 2008/0137074 A1 | 6/2008 | Furman et al. | |
| 2008/0174771 A1* | 7/2008 | Yan et al. | 356/237.5 |
| 2009/0030630 A1 | 1/2009 | Eitan et al. | |
| 2009/0201494 A1 | 8/2009 | Furman et al. | |
| 2009/0323051 A1* | 12/2009 | Matsui | 356/237.3 |

OTHER PUBLICATIONS

Applied Materials South East Asia PTE. Ltd.; Application No. PCT/IL2009/000572 filed Jun. 9, 2009; International Search Report and Written Opinion, ISA/EP, Sep. 16, 2009, 15pp.
Appled Materials South East Asia PTE. Ltd.; PCT/IL2009/000572 filed Jun. 9, 2009; Written Opinion of the International Preliminary Examining Authority; IPEA/EP; dated Jul. 26, 2010; 11pp.
Applied Materials South East Asia PTE. Ltd.; Application No. PCT/IL2009/000572 filed Jun. 9, 2009; International Preliminary Report on Patentability, IPEA/IL, mailed Jul. 10, 2010, 26 pp.

* cited by examiner

*Primary Examiner* — Hoa Q Pham
(74) *Attorney, Agent, or Firm* — SNR Denton US LLP

(57) ABSTRACT

An optical inspection system or tool can be configured to inspect objects using dynamic illumination where one or more characteristics of the illumination is/are adjusted to meet the inspection needs of different areas. For example, the illumination intensity may be increased or decreased as the tool inspects areas of memory and periphery features in a wafer die. In some embodiments, the adjustment can be based on data obtained during a pre-inspection setup sequence in which images taken based on illumination with varying characteristics are evaluated for suitability in the remainder of the inspection process.

20 Claims, 9 Drawing Sheets

Low Illumination

High Illumination

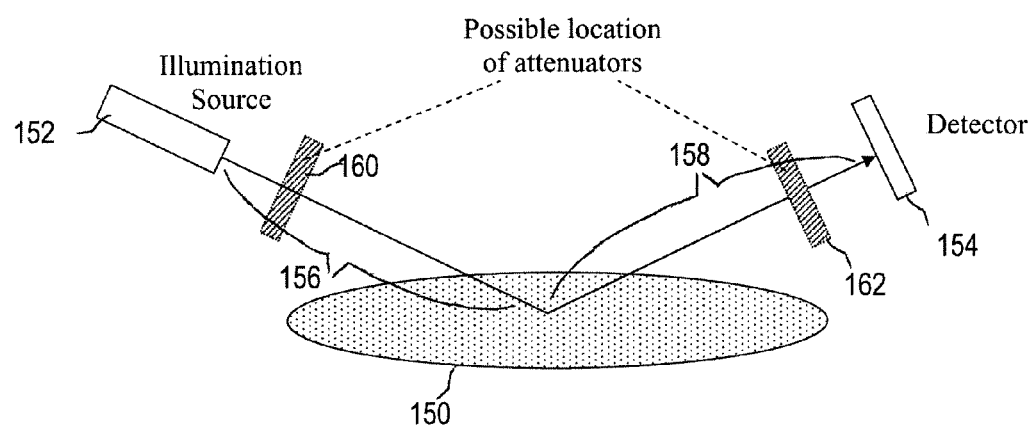
FIGURE 5
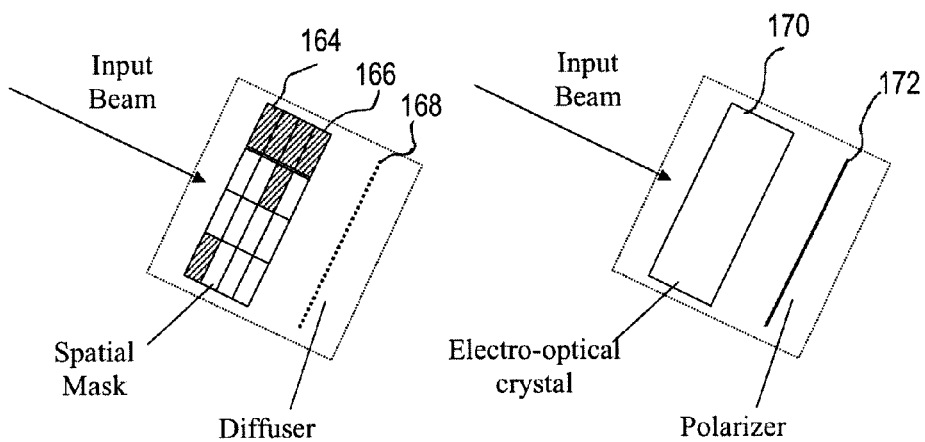
FIGURE 6A  FIGURE 6B

DYNAMIC ILLUMINATION IN OPTICAL INSPECTION SYSTEMS

BACKGROUND

Optical inspection allows for rapid and effective identification of defects in semiconductor objects, which include (but are not limited to) semiconductor wafers, reticles, mask patterns, and other items that are the result of or are used in fabrication of miniaturized electronic devices.

Various illumination and imaging systems have been proposed for optical inspection tools. For example, some systems use lamps or lasers to illuminate the object under inspection, with a detector or an array of detectors used to image areas of interest on the object. The detector output can be analyzed in any number of ways to determine whether a defect exists in the area. However, a semiconductor object oftentimes will comprise areas of different types.

As an example, FIG. 1A shows an example of a wafer die 110 comprising a periphery 112 at the die edges, with an array area 114 in the interior. Wafer die 110 may comprise one of many dies formed on a semiconductor wafer. Periphery 112 may represent logic and I/O circuitry, while array area 114 comprises memory. It should be noted that other dies may have other distributions and types of area, and so this discussion is for purposes of example only.

FIG. 1B shows an array 116 of frames. Some (but not all) inspection tools may logically divide a die or other area of a semiconductor object into a plurality of areas for inspection purposes. "Frames" are one example of such areas. Generally, a "frame" may be a unit imaging area of a tool. For two-dimensional detectors, a frame will comprise an area imaged at a given time (by one or more detectors), while for one-dimensional or point detectors, a frame will comprise cumulative acquired data over a given time period.

In this particular example, array 116 comprises several rectangular frames of the same size and shape. Other tools may use frames of different shape, number, and/or configuration. FIG. 1C shows array 116 overlaid on die 110.

Some inspection tools may comprise one or more detectors, and may inspect an object on a frame-by-frame basis. For example, a tool may image one or more frames of the object and then change its view of the object to image additional frames of different parts of the object. For example, the object may be moved while the tool components remain stationary, the object may remain stationary while some tool components are repositioned, and/or both the position of the object and tool may be adjusted.

Regardless of the underlying inspection methodology, however, the different properties of areas of a semiconductor object may lead to difficulties in inspection. For example, FIGS. 2A and 2B show an example of signal diagrams representing dark-field illumination as reflected from a part of a wafer containing an array and periphery, with defects in both areas. Each diagram also includes an indicator of the saturation limit of the detector, which represents the upper boundary of the detector's dynamic range.

Diagram 120 of FIG. 2A shows the case of illumination that is sufficient to illuminate a defect in the array area, with the defect represented by the signal variance indicated at 124. The defect in the periphery area is represented at 126. In FIG. 2A, the periphery defect 126 (and other periphery signal) is above the saturation limit 122 of the detector. This is because the intensity of reflected light from the periphery area is much higher than the intensity of the reflected light from the array area. In a typical wafer, the ratio between the intensities may reach orders of magnitude.

Diagram 128 of FIG. 2B shows the case of illumination that is set to bring a periphery defect 132 into the dynamic range of the detector (i.e. so that signals from the periphery are below the saturation limit 122). In this case, though, the signal of defect 130 in the array area is much smaller. Thus, the array defect may be difficult or impossible to detect.

Accordingly, there remains a need to provide for optical inspections using sufficient light to view defects without sacrificing inspection quality for other defects.

SUMMARY

In accordance with one or more aspects of the present subject matter, an optical inspection system or tool can be configured to inspect objects using dynamic illumination where one or more characteristics of the illumination is/are adjusted to meet the inspection needs of different areas. For example, the illumination intensity may be increased or decreased as the tool inspects areas of memory and periphery features in a wafer die. In some embodiments, the adjustment can be based on data obtained during a pre-inspection setup sequence described in more detail below.

In some embodiments, an optical inspection tool can comprise an imaging system configured to image at least a portion of a semiconductor object, an illumination source configured to illuminate at least a portion of the semiconductor object, and a control system. The inspection tool can be configured to dynamically adjust the illumination that reaches the semiconductor object during inspection based on data indicating one or more particular characteristics of the illumination. In some embodiments, a particular characteristic comprises an illumination level, and dynamically adjusting the illumination that reaches the semiconductor object comprises changing the intensity of the illumination that reaches the object.

The data upon which the dynamic illumination is based may directly indicate one or more particular desired illumination characteristics for different areas of the wafer. However, the data upon which the dynamic illumination is based may indicate wafer characteristics, and the dynamic illumination can be determined by consulting other data correlating wafer characteristics to desired illumination characteristics (e.g. suitable levels, polarizations, spectra for different types of wafer regions).

In some embodiments, the adjustment is based on data collected by the control system during a pre-inspection setup sequence. The tool may be configured to perform the pre-inspection setup sequence, which can include steps whereby the semiconductor object is imaged at least once and one or more particular characteristics for respective portions of the semiconductor object are determined. In some embodiments, at least two intensities are used during the setup sequence to evaluate which illumination intensities (also referred to as "illumination levels") are appropriate for different areas of the object.

In other embodiments, the data specifying characteristics of the illumination and/or semiconductor object can be obtained in other ways, including by user input, analysis of specification data for the semiconductor object, and/or other analysis of the object.

The illumination that reaches the object can be changed in any suitable manner, including (but not limited to): tuning the source; removing, inserting, and/or adjusting one or more components in an optical path between an illumination source and the semiconductor object (i.e. an "illumination path"); and/or by removing, inserting, and/or adjusting one or more components in an optical path between the semiconductor object and the detector(s) of the imaging system used to image the object (i.e. an "imaging path"). Thus, "dynamic illumination" can include, in some embodiments, situations in which the characteristics of light exiting the source(s) remain unchanged, with characteristics adjusted after actual illumination of the object.

Still further, in some embodiments, the tool can include changeable optics so that some or all light in an imaging and/or illumination path can be diverted into different channels to obtain different characteristics. Dynamically adjusting the illumination can comprise selecting one or more channels to appropriately condition the characteristics of light traveling to and/or from the object.

As noted above, in some embodiments, dynamically adjusting the illumination that reaches the imaging system comprises changing the intensity of the illumination. Dynamically adjusting can additionally or alternatively comprise changing other characteristics, including polarization and/or the spectral band of the illumination. These and any other characteristics can be adjusted independently of one another or in combination.

The tool may further comprise at least one attenuator, with the attenuator used to adjust the illumination that reaches the semiconductor object by placement in the imaging and/or illumination paths. In some embodiments, the attenuator comprises an electro-optical crystal.

In some embodiments, the tool illuminates and images portions of the semiconductor object on a frame-by-frame basis. That is, the area imaged by the tool comprises one or more frames, and the object is imaged by directing the tool to image a first frame (or group of frames), then a second frame (or group of frames), and so on. In such embodiments, dynamically adjusting the illumination can comprise changing the illumination between at least two frames (or groups of frames). In some embodiments, the illumination is adjusted based on evaluating one or more features in the frame.

For example, if illumination intensity is to be varied, the tool may rely on a dynamic range image across the area of interest that can be used to determine what illumination characteristics are suitable. For example, the dynamic range image may comprise reflectivity data for different regions of the area of interest. The dynamic range image or other data may indicate that the frame predominantly includes a particular type of feature (such as array patterns), and the illumination may be adjusted to accommodate the presence of the array. Data other than reflectivity may be used as the basis of a dynamic range image, and other images may be based on factors other than illumination intensity or range.

Some embodiments of an optical inspection tool configured to image at least a portion of a semiconductor object using a plurality of frames can dynamically adjust the illumination of the semiconductor object during inspection so that, for at least one frame that is imaged during an inspection, a first portion of the object imaged in the frame receives a first illumination level and a second portion of the object imaged in the same frame receives a second illumination level. First and second portions of the object imaged in the same frame may receive illumination with other characteristics, such as different polarizations, different spectra, etc.

Still further, the tool can be configured so that first and second portions receive illumination with the same characteristic, but light from the first and second portion is adjusted prior to reaching the imaging system so that characteristics of light from the different portions differs prior to reaching the imaging system.

In some embodiments in which a frame is imaged using multiple detectors, the illumination is adjusted so that each detector is confronted with a constant illumination level. Similarly, if other characteristics are dynamically adjusted, in some implementations, the tool is configured so that such characteristic(s) remain constant across each detector (e.g., if spectrum is changed between frames, each detector may receive light in the same spectral range, etc.).

In some embodiments, dynamically adjusting the illumination of the semiconductor object comprises inserting a controllable spatial mask into the optical path of the illuminating light. The spatial mask may be placed into the illumination path and/or the imaging path. In some embodiments, the spatial mask is imaged onto the object (or detectors, respectively) so that it is out of focus.

In some embodiments, an electro-optical inspection method can comprise illuminating an area of interest of a semiconductor object at a first illumination. For instance, the first illumination may have one or more characteristics of interest, such as an illumination level. The area of interest may comprise, for example, a region of a semiconductor wafer, such as a die, a part of a die, a field on the object, a group of dies or fields, or even the entire wafer. In any event, one or more images of the area of interest can be obtained.

Then, one or more "quality characteristics" can be evaluated for the image. Generally, a "quality characteristic" is a measure of image's suitability for analysis in the inspection. In some embodiments, a quality characteristic comprises the amount of saturation in an image. For example, the percentage of the image that is saturated may be determined.

One or more quality characteristics can be evaluated to determine if the image will be suitable for use, such as by comparing the quality characteristic to a threshold level or other suitable metric ("quality criterion"). For example, the saturation percentage may be compared to a maximum acceptable saturation value.

The illuminating and imaging steps can be repeated with illumination of different characteristics (i.e. second, third, fourth illuminations and so on) based on whether previously-obtained images meet one or more quality criteria. For example, if saturation is a quality characteristic, the illuminating and imaging steps can be repeated at different illumination levels. For example, if the initial illumination level is the maximum available for the tool or suitable for the wafer, then later illumination levels may be lower. The image(s) obtained at the other (in this example) lower illumination can be evaluated for saturation, and the process can repeat until an image having no or negligible saturation is obtained (e.g. below a predetermined threshold).

Based on the image(s), an inspection of the semiconductor object can be performed, where the inspection includes dynamically adjusting the illumination that reaches the object during the inspection based (at least) on the image(s) obtained during the initial steps in which one or more quality characteristics were evaluated. The adjustments may be based directly or indirectly on the images. As noted above, in some embodiments, a dynamic range image can be used. The dynamic range image can comprise data across the area of interest, such as reflectivity data, that indicates what illumination and/or other characteristics are suitable.

In certain embodiments in which illumination intensity level is dynamically adjusted, the data comprising the dynamic range image for each region can correspond to or may be based on the highest illumination intensity for which light from the region did not saturate the detector. For example, if three descending illumination levels were used and a particular region was saturated in all but the final image, then the data for that region in the dynamic range image would be based on the final illumination level. If, for the same sequence, another region was not saturated in the first image, then the data for that region in the dynamic range image would be based on the initial illumination level. In some embodiments, reflectivity data for a region is based on the image value (i.e. the pixel intensity values across the region) divided by an image intensity value for the region, such as the highest intensity of illumination at which the region was not in saturation.

In some embodiments, the method can comprise performing a pre-inspection setup sequence, and then performing an inspection of the semiconductor object, including dynamically adjusting the illumination reaching the imaging components of the tool during the inspection of the area of interest based on the dynamic range image. If the area of interest comprises a die of a semiconductor wafer, then performing an inspection of the semiconductor object can comprise inspecting multiple dies based on the dynamic range image.

An optical inspection method can be based on data obtained outside a setup sequence. For example, in some embodiments, one or more characteristics of illumination are determined during the inspection, such as by consulting data specifying particular types of areas on the object and one or more corresponding illumination characteristics. The areas may be identified based on user input, wafer specification data (i.e. coordinates or structural data that can be used to identify what structures are in the area), and/or analysis of the area by the tool performed during the inspection.

BRIEF DESCRIPTION OF THE DRAWINGS

A full and enabling disclosure including the best mode of practicing the appended claims and directed to one of ordinary skill in the art is set forth more particularly in the remainder of the specification. The specification makes reference to the appended Figures, in which like numerals are intended to represent similar or analogous features.

FIG. 5 is a diagram illustrating potential locations for attenuators for use in a tool that supports dynamic illumination;

FIGS. 6A and 6B are each a diagram showing an exemplary attenuator configuration;

DETAILED DESCRIPTION

Reference will now be made in detail to various and alternative exemplary embodiments and to the accompanying drawings, with like numerals representing substantially identical structural elements. Each example is provided by way of explanation, and not as a limitation. In fact, it will be apparent to those skilled in the art that modifications and variations can be made without departing from the scope or spirit of the disclosure and claims. For instance, features illustrated or described as part of one embodiment may be used on another embodiment to yield a still further embodiment. Thus, it is intended that the instant disclosure includes modifications and variations as come within the scope of the appended claims and their equivalents. The use of headings, numberings, and the like is meant to assist the reader of the specification, and not to limit the subject matter.

Figure 11:
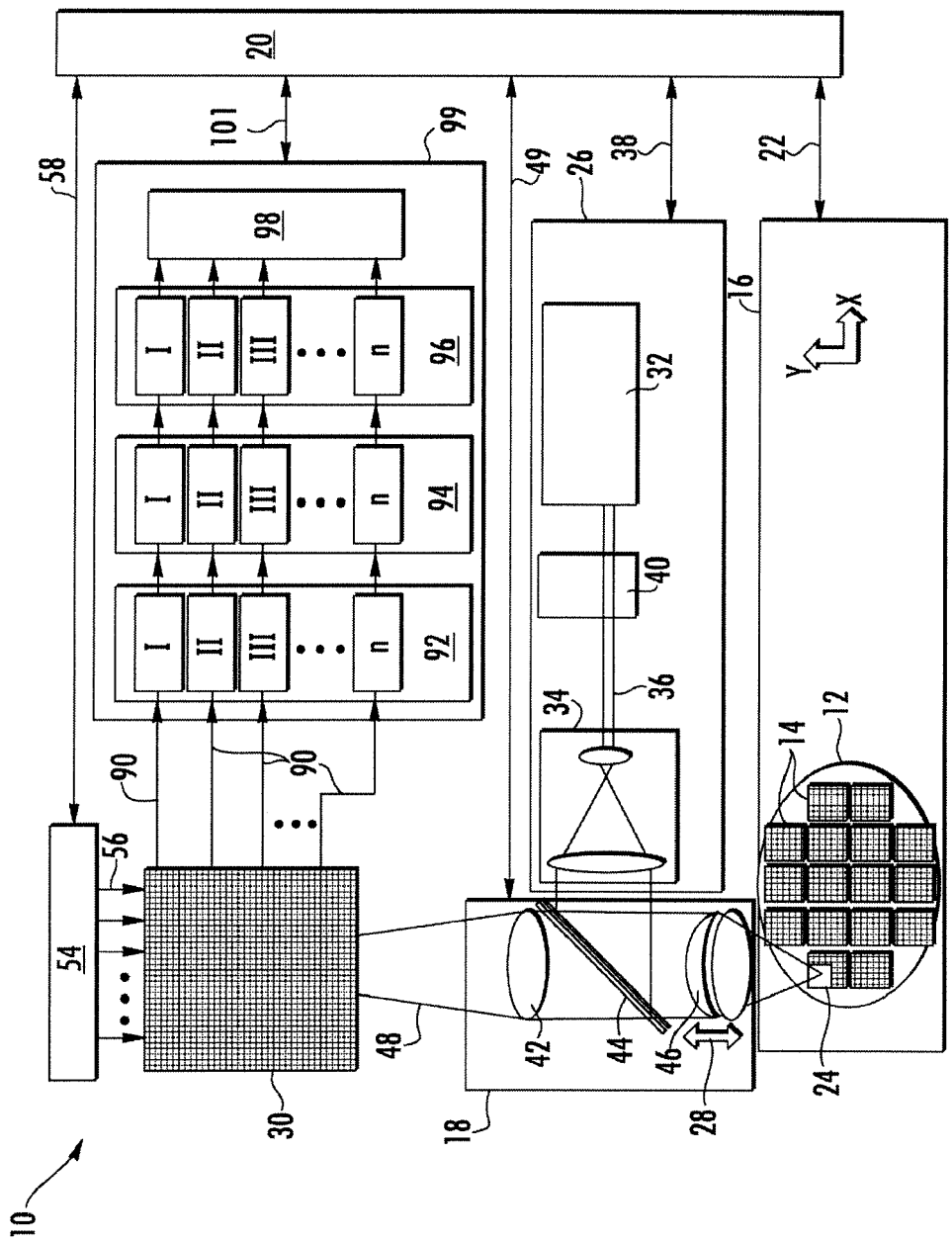
FIG. 11 is a block diagram showing illumination, imaging, and control components in an exemplary optical inspection tool.

Before discussing aspects of dynamic illumination in optical inspection systems, FIGS. 11 and 12 will be discussed to place the illumination in context. FIG. 11 is a block diagram showing illumination, imaging, and control components in an exemplary optical inspection tool and FIG. 12 is a block diagram showing additional aspects of imaging and illumination in an exemplary optical inspection tool.

Figure 12:
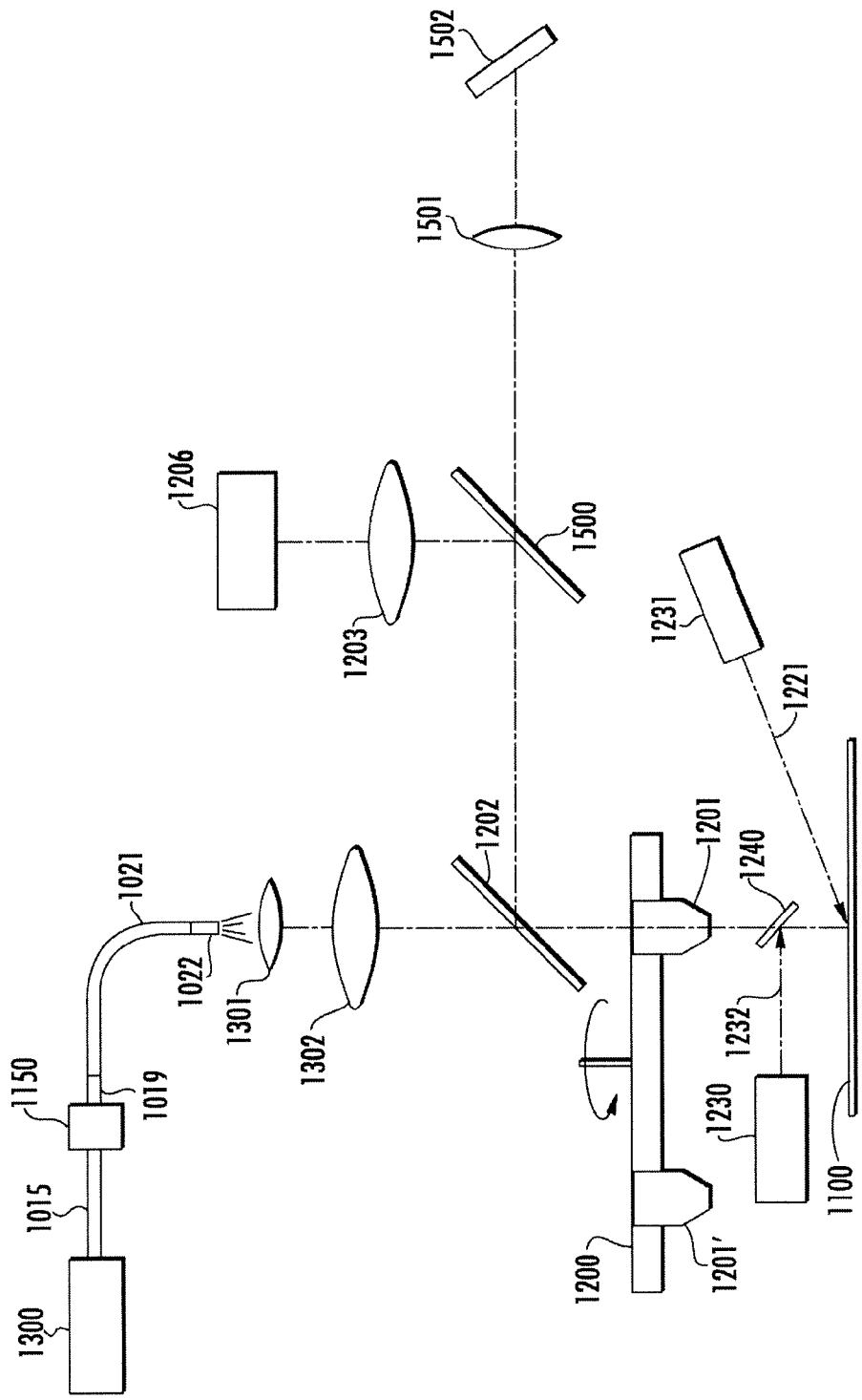
FIG. 12 is a block diagram showing additional aspects of imaging and illumination in an exemplary optical inspection tool.

In this example, FIG. 11 is a schematic diagram illustrating an exemplary embodiment of a system for fast on-line electro-optical detection of wafer defects, while FIG. 12 shows a schematic illustration of an object inspection system utilizing a laser source and a fiber optical delivery bundle in an exemplary inspection tool. For instance, the tool may comprise a Negevtech 3320, 3370, or other model optical inspection tool (available from Negevtech, Ltd. of Rehovot, Israel), modified to support dynamic illumination in accordance with one or more aspects of the presently disclosed detector arrangements and methodologies.

Additional details regarding exemplary aspects of an optical inspection system can be found in U.S. patent application Ser. No. 10/345,097, published as US Patent Application No. 2004-0146295 A1, which is incorporated by reference herein for all purposes in its entirety to the extent it is not in conflict with the present subject matter. However, it is to be noted that the illumination principles discussed herein can be used in any suitable inspection system that creates an image of an object at a focal plane.

As shown in FIG. 11, inspection tool 10 can include a focal plane assembly 30 comprising pixels from multiple two-dimensional detectors. Focal plane assembly 30 is configured so that light from an article being inspected is sensed by detectors arranged in accordance with one or more aspects discussed below so that the tool can support dynamic illumination. In this example, assembly 30 is depicted as providing a continuous surface. It will be recognized that, in different embodiments and depending on the optical configuration and state of the tool, a discontinuous surface may be presented in some instances. Focal plane assembly 30 is interfaced to central control system 20 via focal plane assembly electronics 54 and control/data links 56 and 58.

In operation, the dies 14 of wafer 12 can be illuminated in any suitable manner, such as by laser light from pulsed illumination system 26. Light 48 represents rays of light scattered, reflected, and diffracted by the wafer. This light can be collected using imaging optics 18. In this example, imaging optics 18 comprise a beam splitter 44 (used in illuminating wafer 12 with light from laser system 26), focusing lens 42, an objective lens 46 which may be adjusted using an auto-focus system 28 (not shown in detail), and control/data link 49. In this example, focusing lens 42 focuses light 48 onto focal plane assembly 30 and defines the focal plane of imaging optics 18. However, the actual content and arrangement of a particular set of imaging optics can vary. Particularly, the imaging optics 18 shown in this example are simplified for purposes of explaining general principles of an inspection tool. As will be noted below, in some embodiments of tools that include dynamic illumination, the imaging optics may further comprise attenuators and the like used to adjust illumination.

A patterned semiconductor wafer 12 featuring a plurality of wafer dies 14, is placed and aligned on a continuous moving XY translation stage 16 to impart relative motion between the wafer and the components used to image the wafer. XY translation stage 16 moves wafer 12 typically in a serpentine pattern beneath an optical imaging system 18, thereby changing which area of the wafer is in view of the imager. However, movement patterns other than a serpentine pattern could be used. Additionally, the wafer may be moved in a different manner in other embodiments. Furthermore, in some embodiments, the wafer may remain stationary, with apparent motion between the wafer and component(s) used to image the wafer imparted by the use of one or more optical components. For instance, a rotating mirror can be used to move the field of view of imaging optics 18 in a serpentine (or other) pattern across the wafer. In other embodiments, relative motion may be imparted by moving both the wafer and adjusting optical components.

Movement of XY translation stage 16 (and therefore movement of wafer 12) is synchronized with action of a multi-component camera system by a central control system 20 via control/data links 22, in such a way that wafer 12 moves the equivalent of one field of view 24 during a CCD matrix photo-detector frame time. For example, the frame time and motion may be synchronized so that the wafer moves only on the order of about $10^{-2}$ of a single pixel during exposure to an illumination system 26, thereby resulting in little to no image smear or loss of image resolution. Control system 20 can comprise any suitable type or arrangement of components used to orchestrate the inspection process, including, for example, a microprocessor-based controller, a general-purpose or specialized computer system, and the like.

In this example, illumination system 26 includes a repetitively pulsed laser 32, a laser beam expander 34, a laser beam light path 36, control/data links 38, and a crystal 40 having non linear optical properties and serving as a 'second harmonic' or 'third harmonic' generating crystal. This type of illumination system enables ultra fast imaging of a large field of view 24, by featuring pulsed laser 32 for repetitively generating and propagating a highly bright and highly energetic light pulse in an extremely short period of time. Illumination system 26 is in communication with the central control system 20 via control/data links 38. As will be noted below, in some embodiments, the illumination system can comprise additional components used to adjust the illumination. Furthermore, in embodiments in which the intensity or other aspects of the illumination can be tuned, appropriate control/data links can be used to command desired illumination levels and/or other characteristics from the pulsed laser 32 and other components.

Briefly, FIG. 12 illustrates exemplary components associated with illuminating an object in an inspection system. According to different methods of operation, three alternative modes of illumination can be provided: Bright Field (BF), Side-illuminated Dark Field (DF) and Orthogonal or Obscured Reflectance Dark Field (ODF). Each mode of illumination is used to detect different types of defects in different production process steps. For example in order to detect an embedded defect in a transparent layer, such as silicon oxide, BF illumination may be preferred. In order to detect a small particle on a surface, DF illumination can generally yield better results.

In bright field illumination in general, the illumination is incident on the sample through the same objective lens as is used for viewing the sample. FIG. 12 shows a bright field illuminating laser source 1300 delivering its output beam 1015 into an optical delivery fiber bundle 1021, preferably by means of a laser to fiber coupler 1150. This optical fiber bundle 1021 provides both uniform illumination on the sample and coherence breaking of the laser illumination. In some embodiments, only a single fiber bundle is used, but it is to be understood that a serially-arranged fiber bundle solution may also be suitable. In other embodiments, one or more bundles may be combined with further components, such as a light guide or guides. Discussion of exemplary fiber/light guide combinations can be found in co-pending U.S. patent application entitled "Speckle Reduction Using a Fiber Bundle and Light Guide," Ser. No. 11/503,859, filed Aug. 14, 2006 published as US20080037933A1 on Feb. 14, 2008, which is incorporated by reference herein for all purposes in its entirety to the extent it is not in conflict with the present subject matter.

From the output termination of the fiber bundle 1021, the laser beam is imaged by means of illumination transfer lenses 1301, 1302 onto the objective lens in use 1201, which is operative to focus the illumination onto a wafer 1100 being inspected. Appropriate alternative objective lenses 1201' can be swung into place on an objective revolver 1200, as is known in the microscope arts. The illumination returned from the wafer is collected by the same objective lens 1201, and is deflected from the illumination path by means of a beam splitter 1202, towards a second beam splitter 1500, from where it is reflected through the imaging lens 1203, which images the light from the wafer onto the detectors of the imager, with one of the detectors represented in FIG. 12 at 1206. In this example, only a single detector and optical path is shown for purposes of example. The actual path of light comprising the inspection image will, of course, vary, if components are included in the imaging path; likewise, components for adjusting illumination may adjust the illumination path.

In this example, the second beam splitter 1500 is used to separate the light going to the imaging functionality from the light used in the auto-focus functionality, which is directed by means of the auto-focus imaging lens 1501 to the auto-focus detector 1502.

When conventional dark field illumination is required for the imaging in hand, a dark field side illumination source 1231 is used to project the required illumination beam 1221 onto the wafer 1100. When orthogonal dark field, or obscured reflectance dark field illumination is required for the imaging in hand, an alternative dark field illumination source 1230 is used to project the required illumination beam 1232 via the obscured reflectance mirror 1240 onto the wafer 1100 orthogonally from above. FIG. 12 indicates sources 1300, 1231, and 1230 at different locations. However, any or all of sources 1300, 1230, and 1231 may comprise the same light source, with the bright field, dark field, and obscured reflectance dark field effects achieved through moving the source(s) and/or redirecting illumination to the appropriate angle using one or more optical components. Further, it is to be understood that other arrangements for laser illumination and/or other illumination methods entirely could be used in conjunction with the present subject matter.

In operation, one or more images of the wafer are obtained and the images are analyzed to determine the presence or absence of a defect or potential defect in the wafer. For example, the tool may include an image analysis system comprising one or more computers or other suitable image processing hardware configured to evaluate the images. In the example of FIG. 11, an image processing system 99 includes parallel configured image processing channels 90 for image grabbing by an image grabber 92, an image buffer 94, a defect detection unit 96, a defect file 98, and control/data links 101. Image data acquired by focal plane assembly 30 featuring twenty-four two-dimensional CCD matrix photo-detectors 52 is processed in parallel, whereby each of the twenty-four CCD matrix photo-detectors communicates separately, in parallel to the other CCD matrix photo-detectors of focal plane assembly 30, with image grabber 92, via twenty-four separate image processing channels 90. Instead of processing image data using a single serial channel of 48 megapixels at a CCD frame speed acquisition rate of 60 times per second (resulting in a single channel with a very high, 3 gigapixels per second processing rate), each of the twenty-four or more separate image processing channels 90 having about 2 megapixels of image data, acquired at a rate of 60 times per second, is used for processing at a moderate rate of tens of megapixels per second. Image processing system 99 is in communication with central control system 20 via control/data links 101.

As another example, the tool may be connected to suitable hardware for image analysis, or image data may be provided to such hardware in any other manner.

Any suitable type(s) of analysis may be used to determine the presence or absence of defects. For example, the tool may obtain images on a frame-by-frame basis and compare single frames or groups of frames to references. As another example, the tool may analyze images without comparison to other images, such as locating bright spots on a dark area and/or dark spots on a light area. Any suitable comparison/analysis technique(s) may be used, including cell-to-cell comparison, die-to-die comparison, and may be carried out using any suitable software algorithm(s) and/or specialized hardware to analyze and process the images.

The detectors in the tool can comprise any suitable number, type, or combination of light-sensing elements. The underlying sensing can be based on any suitable technology. For instance, in various embodiments, one or more of the following types of detector types can be used: CCD, CMOS, PMT, and/or avalanche photodiode detectors.

The detectors may be of any suitable type. For example, one or more detectors may comprise an area detector, such as a matrix of photo-sensors producing 2 dimensional image data. As another example, one or more detectors can comprise a TDI line detector, i.e. a matrix of photo-sensors which produces 1 dimensional image data over time. As another example, one or more detectors can comprise a line detector i.e. a line of photo-sensors which produces 1 dimensional line image. In certain embodiments, a detector can comprise a "point detector," where each detector signal represents a pixel.

It will be appreciated that, in some embodiments in which light sensing and imaging is based on point detection, such as when PMT and/or avalanche photodiode detectors are used, the illumination and/or imaging hardware will need to be varied appropriately from the example arrangements discussed above in conjunction with FIGS. 11 and 12. For example, embodiments of a tool using PMT and/or avalanche photodiode detectors can include some sort of scanning mechanism to variably illuminate spots on the wafer or other object(s) under inspection. For instance, a suitable illumination source (such as an argon laser or another laser) can be used in conjunction with an acousto-optical deflector to scan one or more illuminating beams across the wafer or other object(s) under inspection.

As one example of inspecting using a scanning source, a sawtooth pattern in the time domain can be used while the stage moves the wafer orthogonally to the movement of the illuminating beam. The imaging optics can be arranged to appropriately collect light from the illuminating beam as reflected or otherwise scattered by the wafer. Exemplary details of an inspection system including a scanning illumination source can be found in U.S. Pat. No. 5,699,447, which is incorporated by reference herein in its entirety to the extent it does not conflict with the present subject matter. Exemplary discussion of line detection can be found in U.S. Pat. No. 6,724,473, which is incorporated by reference herein in its entirety to the extent it does not conflict with the present subject matter.

When TDI or line detection is used, illumination and relative movement of the wafer should be adjusted accordingly, with the image acquisition hardware/software also suitably configured. For instance, as is known in the art, when TDI detection is used, continuous illumination is applied while the imaging location on the wafer or other object is varied.

The above discussion is for purposes of example only with regard to illumination and imaging techniques. The present subject matter can be utilized in the context of any suitable inspection tool. Next, several different aspects of tools including dynamic illumination will be discussed in closer detail.

Figure 1A:
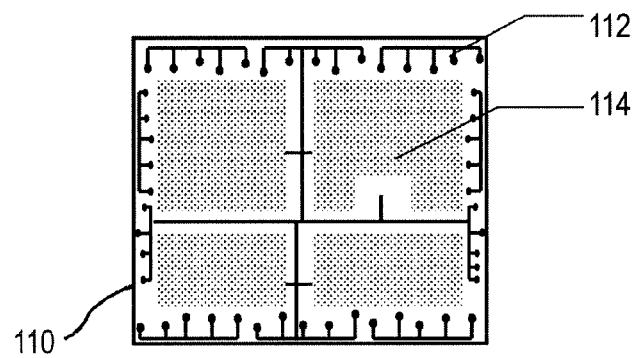
FIGS. 1A, 1B, and 1C are diagrams showing an exemplary semiconductor wafer die and an example of an array of frames that may be used in inspecting the die.
Figure 1B:
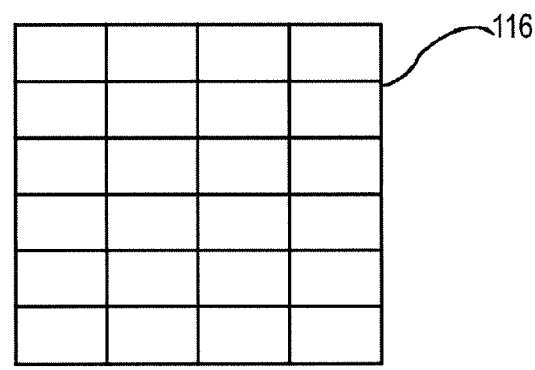
Figure 1C:
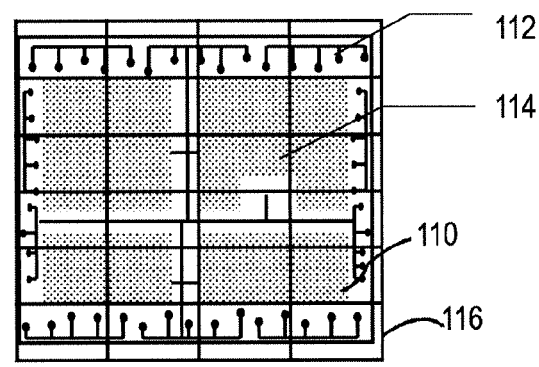
Figure 2A:
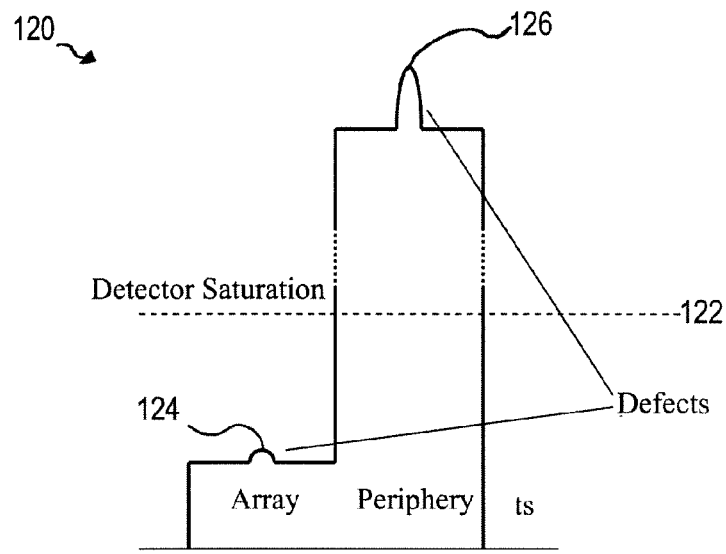
FIGS. 2A and 2B are each a diagram showing the relationship between signals representing defects in different areas and detector saturation.
Figure 2B:
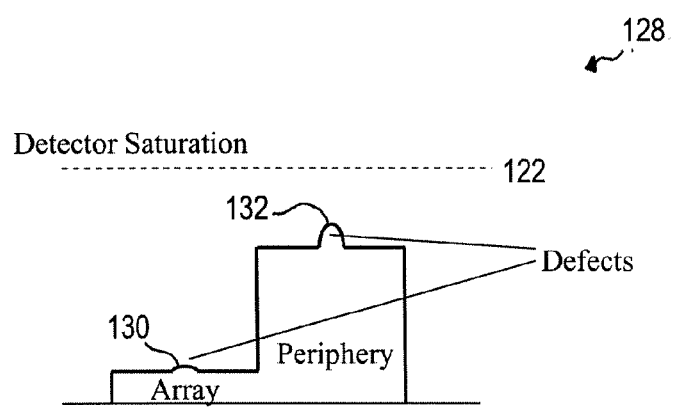
Figure 3:
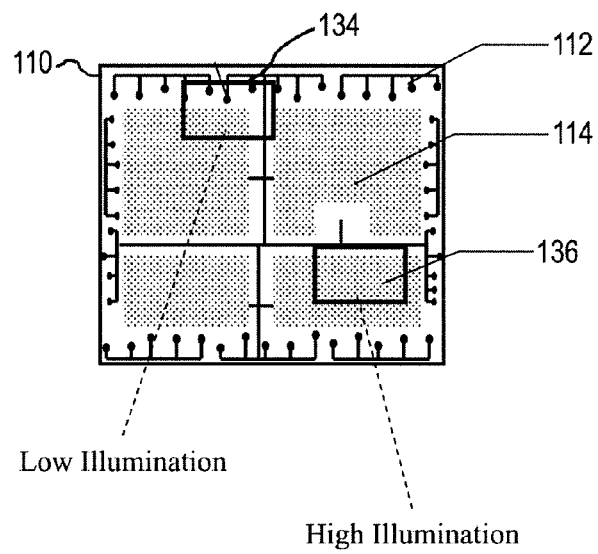
FIG. 3 shows an example of frames that receive different illumination when inspected by an optical inspection tool that supports dynamic illumination.

FIG. 3 is a diagram showing an exemplary die 110 that includes periphery areas 112 and array areas 114. FIG. 3 further depicts two exemplary frames 134 and 136. As was noted earlier, in some embodiments, an inspection tool may perform inspections on a "frame by frame" basis in which the object under inspection is logically divided into one or more frames during inspection. The inspection tool can view only a limited area at any given time (field of view), and so during an inspection, one or more frames are illuminated and imaged in a first field of view, then the field of view is changed and additional frames are illuminated and imaged, and so on. Each frame may be imaged by one or more detectors. Furthermore, frames may be two dimensional as shown in the examples herein, one dimensional (i.e. a line of pixels), or even may constitute a single pixel each. Depending on the particular inspection, some or all of the frames may be contiguous, may overlap, and/or may be spaced from other frames resulting in a gap between frames.

In some embodiments, frames that contain mostly periphery areas, such as frame 134, are inspected using a low level of illumination while frames that contain mostly array areas, such as frame 136, are inspected using a high level of illumination.

The particular manner in which the illumination level is defined can vary. For example, the illumination level may be a function of the predominant characteristics within the frame as noted above. However, in other embodiments, the illumination may be a continuous function of the image data in the frame.

Figure 4:
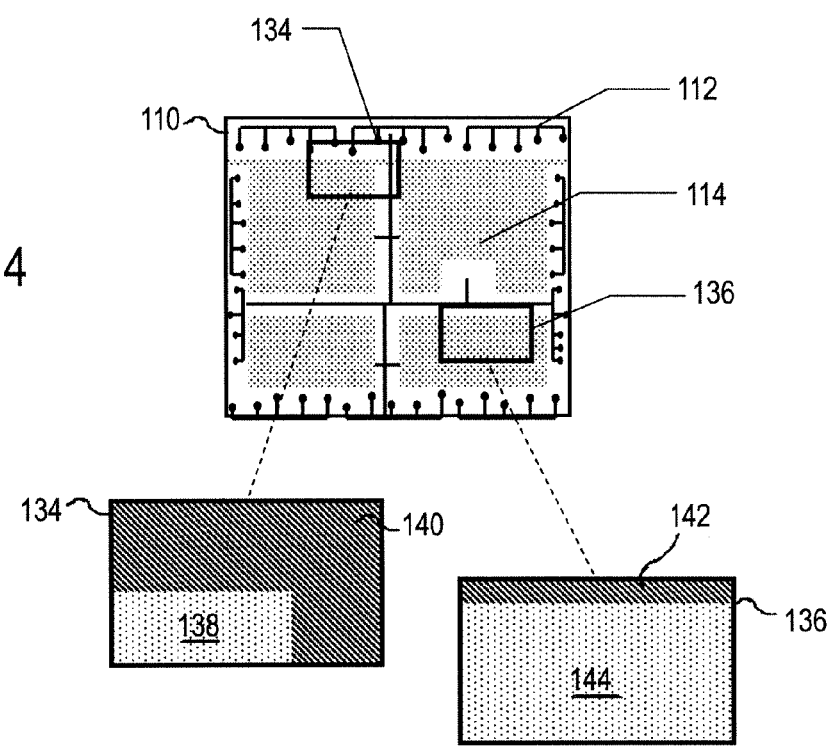
FIG. 4 shows another example of how illumination may differ in a tool that supports dynamic illumination.

FIG. 4 shows another exemplary embodiment. Again, exemplary die 110 and frames 134 and 136 are shown. In this example, though, dynamic illumination is used by the tool for different regions within frames as appropriate. Put another way, the illumination is adjusted at a higher resolution than the example of FIG. 3, where the illumination was adjusted at the frame level. In this example, illumination is adjusted at the sub-frame level, particularly based on regions within each frame.

FIG. 4 includes a close-up view for frames 134 and 136. Each frame of this example includes two different regions, although of course in other embodiments, a frame could contain more or fewer regions than two. Frame 134 includes region 140, which contains periphery structures and region 138, which includes array structures. Frame 136 includes periphery region 142 and array region 144. In this example, all of the regions are rectangular, but region size and shape can vary.

Regardless of the region configuration, each region can receive a particular level of illumination. For example, when frame 134 is inspected, region 140 can receive a lower level of illumination than region 138. Similarly, region 142 may receive a lower level of illumination than region 144. The illumination levels of regions 138 and 144 may be the same or may differ depending on the particular characteristics of the regions as determined by a pre-inspection setup phase.

Illumination can be adjusted in any suitable manner. FIG. 5 is a block diagram showing an example wherein a variable attenuator is placed in an optical path of the illumination. In this example, semiconductor object 150 (a wafer in this example) is illuminated by source 152, with light scattered by object 150 detected by detector 154. This example also shows illumination path 156 between the source and the object and imaging path 158, which is traveled by light moving from the object to the one or more detectors 154. A single detector is shown in this example for purposes of explanation, but of course multiple detectors could be used (or even multiple illumination sources as appropriate). FIG. 5 shows two example locations for a variable attenuator—in this example attenuator 160 in the illumination path and an attenuator 162 in the imaging path. An attenuator could be placed in either or both paths. Moreover, multiple attenuators could be used in a single path.

In practice, the variable attenuator should be able to change the attenuation fast enough for operation of the tool. For example, if the tool images 30 frames per second and attenuation is to be changed between each frame, then the attenuator should be capable of changing between frames (i.e. a response time better than 1/30 of a second).

It will be appreciated that attenuators can be placed in other optical paths in the tool as needed. For example, in a tool with an auto-focus arrangement, one or more attenuators can be placed in the imaging or illumination path of the auto-focus arrangement.

FIGS. 6A and 6B provide examples of structures for fast attenuation. FIG. 6A depicts a spatial mask, such as an LCD array, micro shutter array, or micro mirror array, combined with a diffuser. In embodiments using a micro mirror array and diffuser, the mirror array should generally be placed at an angle to the incoming beam, with the diffuser located in the path of the illumination reflected by the mirror array. In FIG. 6A, several rows of variable pixels 164, 166 are shown, along with diffuser 168. In this example, the number of transmissive or reflective pixels at the spatial mask determine the entire attenuation.

In FIG. 6B, another example is shown. This variable attenuator comprises an electro optical crystal 170, such as a Kerr cell or Pockels cell, and a polarizer 172. If the input beam is not polarized, another polarizer may be placed before the variable attenuator.

In both FIGS. 6A and 6B, appropriate control/data lines and connections can be included for proper control of the attenuator characteristics by the inspection tool control system(s).

Not all embodiments need to use an attenuator. For example, instead of attenuators, the intensity of the illumination source itself may be tuned. For example, if the source comprises a laser, the source voltage may be varied. If the source comprises a Q-switched laser, the intensity can be varied by changing the Q-switch delay time. Other laser illumination sources with adjustable intensity may be adjusted accordingly.

Still further embodiments can dynamically adjust illumination by source tuning and attenuators.

Figure 7:
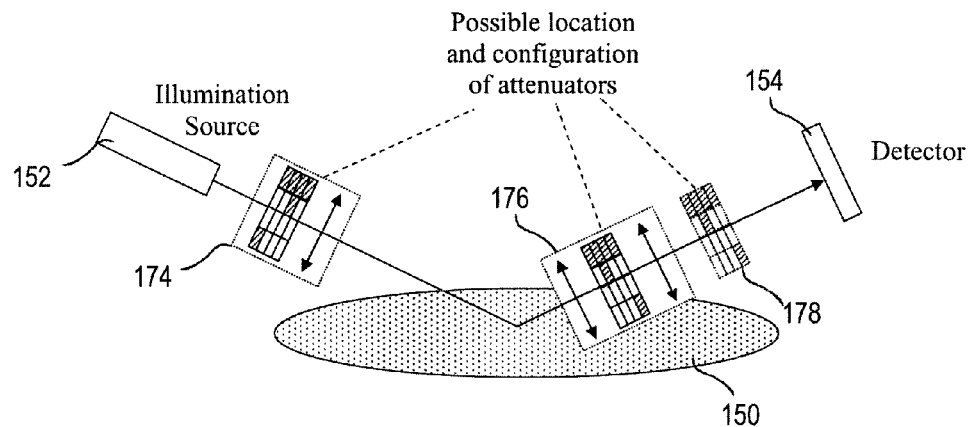
FIG. 7 depicts an example of several different attenuator locations and configurations.

FIG. 7 provides another example of the use of attenuators which may be particularly useful in embodiments in which illumination is dynamically adjusted for different regions within the same frame. FIG. 7 again shows source 152, detector 154, and object 150. In this example, attenuators 174, 176, and 178 are shown in various positions in the imaging and illumination paths. Attenuator 174 is located in the illumination path and comprises a variable spatial mask in this example. For instance, attenuator 174 may comprise an LCD array, micro shutter array, or micro mirror array. The micro mirror array, if used, may be placed at an angle to the incoming beam and commanded so that desired light is reflected to continue on the path, while non-desired light is reflected away from the path and/or passes through the array.

In order to dynamically adjust illumination for different regions within the same frame, a pixilated attenuator should be used. Furthermore, the attenuator should be imaged onto the wafer (if placed in the illumination path) or imaged onto the detector (if placed in the imaging path).

Figure 8:
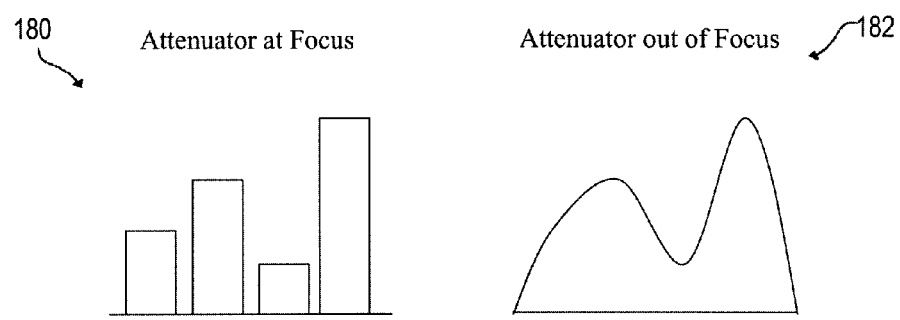
FIG. 8 provides two diagrams showing exemplary results of focusing an attenuator differently.

FIG. 8 illustrates two example signal diagrams 180 and 182 in order to point out a consideration for when pixilated attenuators are used. Diagram 180 represents received illumination when the attenuator is focused-namely, the illumination is non-continuous, and in fact includes gaps with no illumination. This is due to the fact that the fill factor of the pixilated attenuator is not 1. On the other hand, diagram 182 indicates how, when the attenuator is out of focus, the illumination is continuous and without gaps. Accordingly, in some embodiments, the variable spatial mask and its corresponding optics can be placed so that the attenuator will be out of focus. As an alternative, the tool can be configured to compensate for the focus condition of the attenuator by including appropriate components such as lenses, for example, to adjust the focus of light entering and/or exiting the attenuator.

Figure 9:
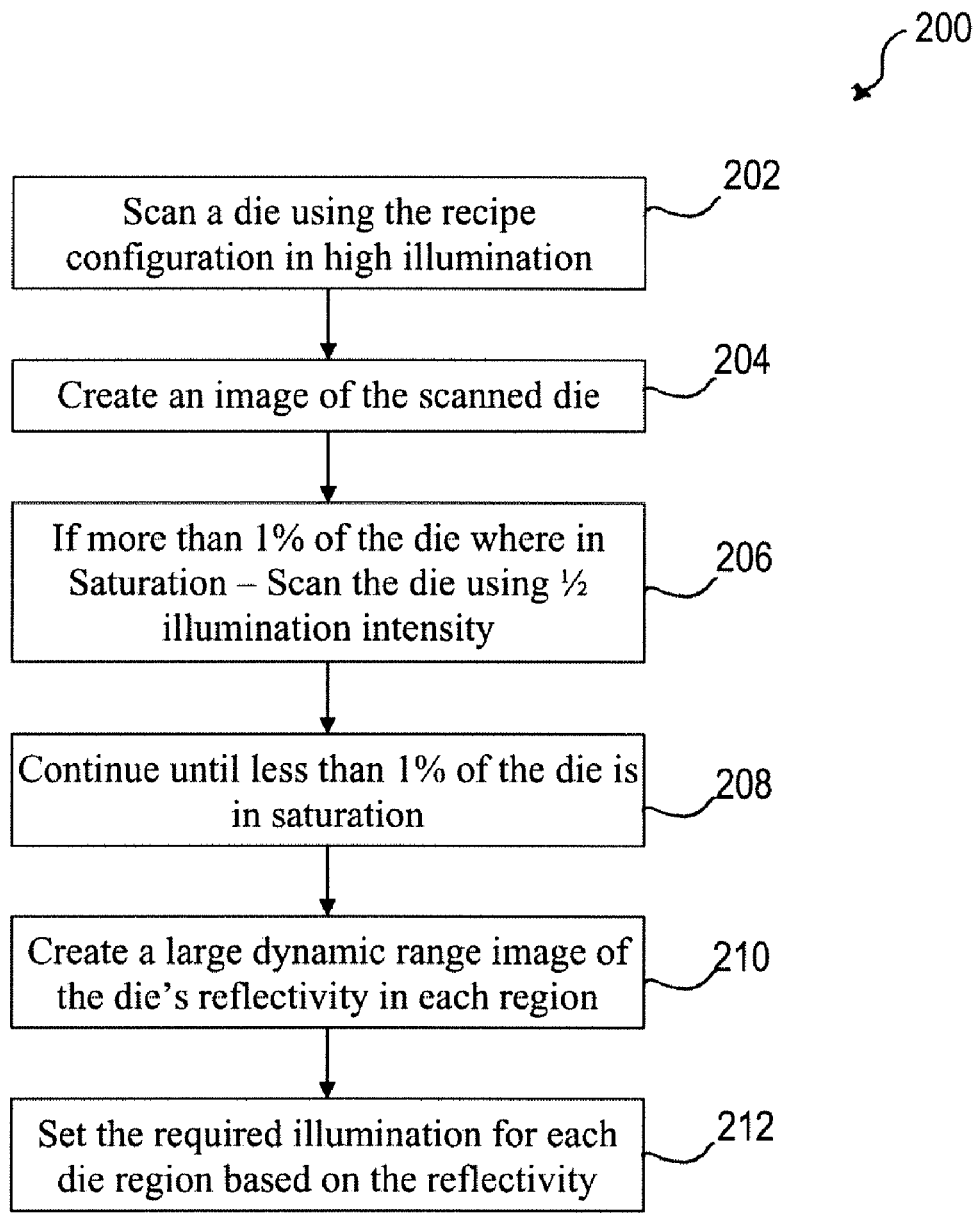
FIG. 9 is a flowchart illustrating steps in an exemplary optical inspection method including a pre-inspection setup sequence.

FIG. 9 is a flowchart showing steps in an exemplary method 200 of optical inspection. This example discusses particular aspects of a pre-inspection setup sequence. At 202, a die or other area of interest is scanned using a high level of illumination. Notably, the inspection recipe may specify only certain areas of a die or wafer for inspection, and so if less than an entire die (or other area) is to be inspected, then the pre-inspection sequence may proceed only as to the portion(s) to be inspected. Although in this example the area of interest is a die, in other embodiments, a field, a group of dies or fields, a part of a die, or even an entire wafer may be analyzed during the pre-inspection setup sequence.

At step 204, an image of the scanned die (or other area of interest) is created by using the detectors of the inspection tool. When the first scan is carried out using the highest illumination available for the tool (or suitable for the wafer), some or all of the image may be saturated.

In any event, though, at step 206, the image of the area of interest is analyzed to determine if the saturation in the image exceeds a predetermined amount. Saturation in the image can be detected in any suitable manner, and generally will be indicated by data showing that the detector reached its maximum range over a particular area. For example, the saturated area may be indicated as bright white. Of course, the detectors may be configured to provide an explicit indication of saturation. In this particular example, the die image is analyzed to determine if more than one percent of the die is in saturation.

Step 206 also represents selection of another intensity level if the saturation in the image exceeds a predetermined amount. In this example, the illumination intensity is halved. Step 208 indicates that steps 202, 204, and 206 are repeated until the image of the die contains less than the predetermined threshold of saturation. In this example, the die is scanned, imaged, and analyzed until the analysis shows that less than one percent of the die image is in saturation, with the illumination intensity halved in each iteration.

Step 210 represents creation of a dynamic range image of the die's reflectivity in each region. This image can be computed based on the one or more images obtained during steps 202, 204, and 206 and iterations of those steps at different power levels.

The one or more images are analyzed to determine, for the various regions of the die (or other area of interest), which illumination level resulted in non-saturated images of the region. Particularly, the highest illumination intensity that did not saturate the image of the region is identified. The dynamic range image can comprise a plurality of pixels each corresponding to a reflectivity value for a pixel in the region, with the reflectivity values comprising the image value divided by the identified illumination intensity at which the region containing the pixel was not saturated.

Step 212 represents actions that may occur during an inspection following the pre-inspection setup sequence. Particularly, for each region, the appropriate illumination level can be selected based on the data in the dynamic range image. For example, the reflectivity of the largest area in the frame or region can be found, with the illumination value comprising a constant divided by the reflectivity. Thus, as the reflectivity increases, the illumination value decreases.

In practice, the dynamic range image can be accessed during an inspection and used to ascertain the appropriate illumination level for an area about to be imaged. In other embodiments, the entire dynamic range image can be evaluated to obtain a set of illumination levels which are then consulted as the inspection progresses. The determined illumination levels can be presented to an operator through a suitable interface (e.g. display screen, printout, etc.) for fine-tuning by an operator.

In other embodiments, other representations of the optical characteristics can be used in addition to or instead of reflectivity, or reflectivity can be derived by methods other than those discussed in the present examples.

Generally speaking, the dynamic range image can comprise data representative of one or more properties of the die (or other area of interest) that can be used as a basis for determining illumination levels.

In various embodiments, the illumination may be up-limited or down-limited. For example, if the dynamic range image data (and/or other data) indicates that an area includes array structure, the illumination may be down limited to ensure that the detection sensitivity for the array area is not negligible—that is, the illumination intensity can be subjected to a floor that ensures enough illumination is provided to sufficiently detect defects in the array area. As another example, if the dynamic range image data (and/or other data) indicates that a particular area includes periphery, then the illumination may be subjected to an upper limit to ensure that illumination of the periphery area will not saturate pixels used to image the nearby array area.

Illumination may be adjusted based on other inspection and tool parameters. For example, some tools "bin" pixels of detectors in different situations. See, for example, U.S. patent application Ser. No. 11/781,454 by Giora Eitan and Shai Silberstein, filed Jul. 23, 2007, entitled "Optical Inspection Tool Featuring Multiple Speed Modes," and published as US 2009/0030630 A1. application Ser. No. 11/781,454 is incorporated by reference herein in its entirety to the extent it is not in conflict with the present subject matter.

Briefly, the full resolution of the inspection tool may not always be required depending, for example, on the nature of the area of the object being inspected and/or the requirements of a particular defect determination technique. For example, as was noted above, a tool may operate in dark-field inspection mode, such as when inspecting memory areas of a wafer or die. The use of Fourier filtering may advantageously increase the probability of detecting a defect in an area by filtering out repetitive patterns in the area so that any defect will stand out. Therefore, lower resolution may be used for such an inspection. Similarly, many defects of great importance may be large enough to stand out at relatively low magnification/resolution. Therefore, in some inspection tools, some of the pixels that are used to obtain inspection images may be binned.

Binning can be achieved in any suitable way. For instance, pixels may be binned in software, hardware, or using both software and hardware. However, hardware-based binning, especially binning at the detector, may be advantageous in some systems. As an example, binning of a plurality of pixels may be implemented by averaging the charge from pixels at the detector.

For instance, when a binning of 1:2 is applied (i.e., two pixels in the detector are binned and treated as a single pixel), the illumination may be halved relative to the illumination level used in the non-binned state. If a binning of 1:4 is applied, the illumination may be 25% of the non-binned illumination, and so on. The illumination may not necessarily be a direct function of the binning state—for instance, a binning of 1:3 may be applied, but the illumination is 27% of the illumination used in the non-binned state.

The particular source or type of illumination can vary. For example, although several examples herein pertain to laser illumination, other illumination sources, such as lamps, could be suitably attenuated. Furthermore, the dynamic illumination principles discussed herein could be applied for bright field, dark field, orthogonal dark field, or any other suitable type of illumination. Broadband or narrowband illumination could be used, as appropriate. The attenuators and other optical components should, of course, be configured to appropriately attenuate light at the wavelengths provided by the source and/or detected by the optical inspection tool.

Additional exemplary detail regarding broadband illumination can be found in U.S. patent application Ser. No. 11/684,191, filed Mar. 9, 2007 and entitled "Wafer Inspection Using Short-Pulsed Continuous Broadband Illumination" (published as U.S. Patent Application No. 2007/0273945 A1), which is incorporated by reference in its entirety herein to the extent it is not in conflict with the present subject matter.

When broadband illumination is used, additional options may be available. For instance, instead of, or in addition to, changing the illumination intensity, the illumination spectrum may be changed to better accommodate the characteristics of particular areas of the semiconductor object. For example, returning briefly to FIG. 5, elements 160 and/or 162 could be replaced with a controllable spectral attenuator. Replacement of element 160 with such an attenuator could allow the illumination spectrum to be changed for each frame, while replacing element 162 could allow for the spectrum of imaged data to be controlled. As another example, spectrum could be changed for each region in addition to or instead of each frame, such as by replacing one or more of elements 174, 176, and/or 178 with a pixilated spectral attenuator.

Controllable spectral attenuators can be implemented in any suitable manner, such as by using acousto-optical modulators with suitable control signals provided by the inspection tool controller. Pixilated spectral attenuators could be implemented by a matrix of such modulators.

Regardless of the illumination type, in some embodiments, polarization of the illumination can be changed in addition to or instead of changing illumination intensity (and/or waveband, if available). Elements 160 and/or 162 of FIG. 5 could be replaced by controllable polarizers to control the polarization of the illumination and imaged data, respectively. In some instances, it may be preferred to use both variable polarizers so that cross polarization can be used as needed (i.e. so the imaging polarization can be made orthogonal to illumination polarization). Polarization could be changed for regions and not frame-wide by replacing elements 174, 176, and/or 178 with pixilated controllable polarizers.

Controllable polarizers can be implemented, for example, by using electro-optical crystal structures such as Kerr cells or Pockels cells and in conjunction with a polarizer. Pixilated controllable polarizers could be implemented by a matrix of such crystals and a polarizer. Another example is a liquid crystal or liquid crystal display as an array of polarizing elements.

The term polarizer is meant to refer to any element(s) that can change the polarization state of light by means of absorption, reflection, scattering, imparting phase differences and/or by any other technique. Any particular polarizations can be used as suitable, including circular, elliptical, and linear polarization.

In various embodiments, an optical inspection tool can adjust factors including illumination intensity, polarization, illumination spectrum alone or in combination through use of variable optics including suitable components. The optics may be adjusted to reduce/avoid saturation and/or on the basis of other factors.

Figure 10:
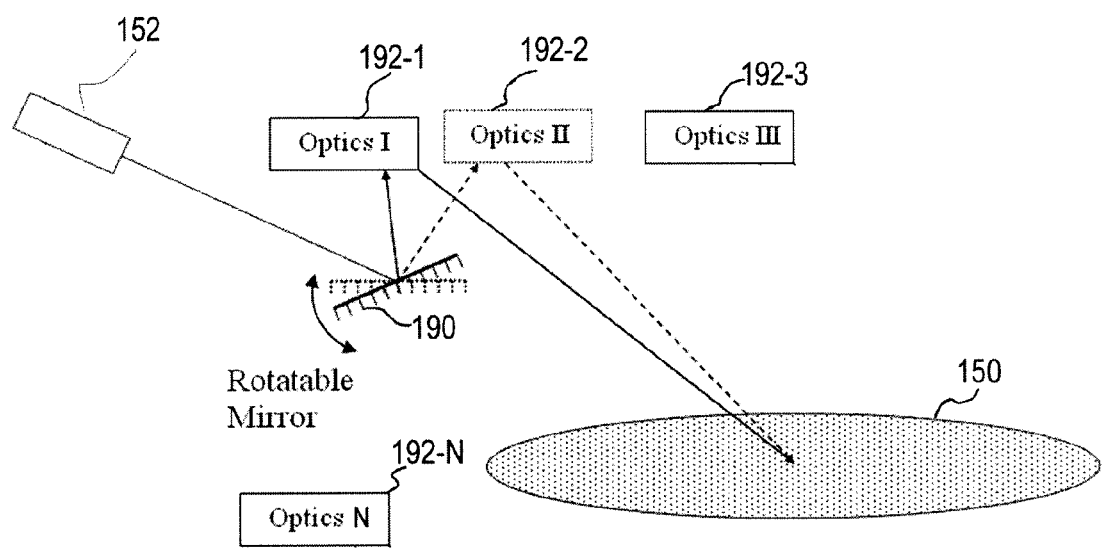
FIG. 10 is a diagram illustrating an example of adjusting illumination by selecting amongst multiple channels in an inspection tool.

In some embodiments, variable optics may be implemented in a tool that supports multiple optical channels. FIG. 10 is a block diagram showing an example of a tool with multiple optical channels. Several channels 192-1, 192-2, 192-3, and 192-N are shown, along with source 152 and semiconductor object 150. In this example, selection mechanism 190 is depicted as controllable rotatable mirror in the illumination path. The tool can select different illumination characteristics by adjusting the rotatable mirror to direct light to a particular channel 192.

Each channel 192 comprises optics which affect light to achieve desired characteristics, including desired attenuation, polarization, spectral effects, and/or other characteristics. Each channel 192 in this example is further configured to direct light towards semiconductor object 150 after passing through its respective optics.

In the example of FIG. 10, each channel directs outgoing light along a different optical path. However, in other embodiments, light from the various channels could be combined into a single optical path by additional components (not shown in FIG. 10) prior to being directed towards object 150.

Additionally or alternatively, channel selection could occur in the imaging path to allow selection between sets of optics which adjust the characteristics of light before the light impinges on the detector or detectors of the tool.

FIG. 10 depicts channel selection mechanism 190 as a rotatable mirror. However, other suitable components controllable to redirect light could be used. For example, a micro mirror array could be used to redirect different portions of light to different channels.

Selection mechanism 190 could be used to select different channels for an entire inspection. However, in some embodiments, a tool is configured to determine if different channels for different frames are needed and to change channels between frames as appropriate. In some embodiments, regions within a frame can be sent to different channels, such as if a micro array (or other structure that can partially redirect light in the same beam to different areas) is used.

The basis for dynamically adjusting the illumination (whether intensity, polarization, spectrum, or other characteristic(s), either alone or in combination) can vary. As noted above, a pre-inspection setup sequence may be used to evaluate characteristics, such as saturation, of a wafer. However, the illumination may be dynamically adjusted based on data obtained in additional or alternative ways.

For instance, illumination and/or imaging parameters may differ based on identification of areas of the wafer (e.g. wafer coordinates for periphery, memory, or other areas). As one example, a user may specify particular illumination conditions for different areas. As another example, the tool may access predefined parameters setting forth illumination conditions based (at least in part) on identification of different areas.

The areas themselves may be set by the user and/or may be determined automatically or semi-automatically. For instance, design data or specifications for the wafer may be input or provided to the tool, with the different areas identified as memory, periphery, etc. in the design data and/or by user input.

The illumination level and/or other characteristics may be determined at the same time as areas are identified, or may be determined at the time of inspection based on data about the areas on the semiconductor object.

As yet another example, the tool can image the wafer and evaluate the image(s) to identify different areas. For instance, one or more aspects of the "pre-inspection" sequence can be performed during the inspection. As an example, the inspection may begin with the tool imaging a first area of interest (e.g., a die) and evaluating one or more illumination characteristics based on the image taken during the inspection. Inspection of subsequent areas of interest (e.g. other dies) can be based on data obtained from the first area of interest (which may or may not be imaged again).

Several examples herein discussed different illumination for periphery and memory areas of wafers. It should be noted that this is not intended to be limiting. For example, wafers with regions of other structures may be associated with other illumination conditions different from the illumination required for memory and periphery areas. Thus, it should be understood that the present subject matter is applicable regardless of the type or name of an area on a wafer.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

The invention claimed is:

1. An optical inspection tool comprising:
an illumination source configured to illuminate a semiconductor object; and
an imaging system configured to image the illuminated semiconductor object,
wherein the inspection tool is configured to, during a pre-inspection setup sequence, obtain a first image of the semiconductor object at a first illumination condition and obtain a second image of the semiconductor object at a second illumination condition, the first illumination condition being different than the second illumination condition, and
wherein the inspection tool is further configured to, during an inspection of the semiconductor object, dynamically adjust an illumination that reaches the imaging system by selecting an illumination level based on the first and second images.

2. The tool set forth in claim 1, wherein the tool is configured to dynamically adjust the illumination by changing an intensity of the illumination.

3. The tool set forth in claim 1, wherein the tool is configured to dynamically adjust the illumination by changing a polarization state of the illumination.

4. The tool set forth in claim 1, wherein the tool is configured to dynamically adjust the illumination by changing a spectrum of the illumination.

5. The tool set forth in claim 1, further comprising at least one attenuator positioned in an optical path between the illumination source and the semiconductor object, wherein the attenuator is configured to adjust an illumination that reaches the semiconductor object.

6. The tool set forth in claim 5, wherein the attenuator comprises an electro-optical crystal.

7. The tool set forth in claim 1, wherein the tool is configured to dynamically adjust the illumination by tuning the illumination source.

8. The tool set forth in claim 1, wherein the tool is configured to utilize at least two different intensities to illuminate the semiconductor object during the pre-inspection setup sequence.

9. The tool set forth in claim 1, wherein the tool is configured to illuminate and image portions of the semiconductor object on a frame-by-frame basis, and is configured to dynamically adjust the illumination by changing the illumination between at least two frames.

10. The tool set forth in claim 9, wherein the tool is configured to dynamically adjust the illumination based on evaluating one or more features in one or more of the frames.

11. The tool set forth in claim 1, further comprising a controllable polarizer positioned in at least an optical path between the illumination source and the semiconductor object or an optical path between the semiconductor object and the imaging system.

12. The tool set forth in claim 1, further comprising a controllable attenuator positioned in at least an optical path between the illumination source and the semiconductor object or an optical path between the semiconductor object and the imaging system, the controllable attenuator configured to attenuate a portion of the illumination's spectrum.

13. An optical inspection tool comprising:
an illumination source configured to illuminate a semiconductor object;
an imaging system configured to image the illuminated semiconductor object using a plurality of frames; and
a controllable spatial mask positioned in an illumination path between the illumination source and the semiconductor object, the controllable spatial mask configured to dynamically adjust an illumination of first and second portions of one of the frames to first and second illumination levels, respectively,
wherein,
the first and the second portions are different from one another and the first and second illumination levels are different from one another,
the inspection tool is configured to perform a pre-inspection setup sequence in which a first image of the semiconductor object is obtained at the first illumination level and a second image of the semiconductor object is obtained at the second illumination level, and
the inspection tool is configured to determine particular illumination levels to be used during an inspection of the semiconductor object for respective portions of the semiconductor object based on the first and second images.

14. The tool set forth in claim 13, wherein the spatial mask is imaged on the semiconductor object out of focus.

15. An electro-optical inspection method comprising:
performing a pre-inspection setup sequence including:
(i) illuminating with an illumination source of an inspection tool an area of interest of a semiconductor object at a first illumination condition;
(ii) obtaining with an imaging system of the inspection tool an image of the area of interest illuminated at the first illumination condition;
(iii) evaluating at least one quality characteristic of the image; and
(iv) performing steps (i), (ii), and (iii) at a second illumination condition instead of the first illumination condition, the second illumination condition being different than the first illumination condition; and
inspecting the area of interest of the semiconductor object, wherein the inspection includes dynamically adjusting an illumination that reaches the imaging system of the inspection tool by selecting an illumination level based on the images obtained during the imaging at the first and second illumination conditions.

16. The method set forth in claim 15, wherein the at least one quality characteristic comprises an amount of saturation in an image, and the first and second illumination conditions comprise illumination at different intensities.

17. The method set forth in claim 16, further comprising creating a dynamic range image of the area of interest from images obtained during the imaging at the first and second illumination conditions, wherein the dynamic range image is used to adjust a level of illumination used during the inspection of the area of the interest.

18. The method set forth in claim 17, wherein creating the dynamic range image of the area of interest comprises:

for each region of the area of interest in the obtained images, determining a highest illumination intensity at which the region was imaged where the region is not in saturation in the image; and for each region, dividing pixel values for the region by the respective highest intensity value at which the region was not in saturation.

19. The method set forth in claim 17, wherein dynamically adjusting the illumination comprises:

for a region of the semiconductor object, determining, from the dynamic range image, a reflectivity of an area of the region; and determining an illumination level for the region based on the reflectivity.

20. The method set forth in claim 15, wherein the area of interest comprises a die of a semiconductor wafer and wherein inspecting the area of interest of the semiconductor object comprises inspecting multiple dies based on a dynamic range image of the die.

* * * * *

UNITED STATES PATENT AND TRADEMARK OFFICE
CERTIFICATE OF CORRECTION

| | | |
|---|---|---|
| PATENT NO. | : 7,973,921 B2 | Page 1 of 1 |
| APPLICATION NO. | : 12/145708 | |
| DATED | : July 5, 2011 | |
| INVENTOR(S) | : Shai Silberstein and Tsafrir Avni | |

It is certified that error appears in the above-identified patent and that said Letters Patent is hereby corrected as shown below:

On the title page, item [73] Assignee:

- Applied Materials South East Asia Pte Ltd. Sinapore (SG) should read -- Applied Materials South East Asia Pte Ltd. Singapore (SG) --

Signed and Sealed this
Twenty-second Day of November, 2011

David J. Kappos
*Director of the United States Patent and Trademark Office*